(12) United States Patent
Steenhoek (10) Patent No.: US 12,044,621 B2
(45) Date of Patent: Jul. 23, 2024

(54) METHOD AND SYSTEM FOR MATCHING COLOR AND/OR APPEARANCE OF A SURFACE

(71) Applicant: AXALTA COATING SYSTEMS IP CO., LLC, Wilmington, DE (US)

(72) Inventor: Larry Eugene Steenhoek, Ellicott City, MD (US)

(73) Assignee: AXALTA COATING SYSTEMS IP CO., LLC, Wilmington, DE (US)

( * ) Notice: Subject to any disclaimer, the term of this patent is extended or adjusted under 35 U.S.C. 154(b) by 75 days.

(21) Appl. No.: 17/815,576

(22) Filed: Jul. 28, 2022

(65) Prior Publication Data

US 2024/0035969 A1    Feb. 1, 2024

(51) Int. Cl.
*G01N 21/57* (2006.01)
*G01N 21/25* (2006.01)
*G01N 33/208* (2019.01)

(52) U.S. Cl.
CPC ........... *G01N 21/57* (2013.01); *G01N 21/251* (2013.01); *G01N 33/208* (2019.01)

(58) Field of Classification Search
CPC .. G01N 21/57; G01N 21/51; G01N 2021/575; G01J 3/463
See application file for complete search history.

(56) References Cited

U.S. PATENT DOCUMENTS

| | | | |
|---|---|---|---|
| 4,917,495 A | 4/1990 | Du Pont | |
| 7,145,656 B2 | 12/2006 | Du Pont | |
| 7,639,255 B2 | 12/2009 | Du Pont | |
| 7,743,055 B2 | 6/2010 | Du Pont | |
| 7,747,615 B2 | 6/2010 | Du Pont | |
| 7,911,615 B2 | 3/2011 | Du Pont | |
| 8,065,314 B2 | 11/2011 | Prakash et al. | |
| 8,270,699 B2 | 9/2012 | Rodrigues et al. | |
| 8,441,641 B1 | 5/2013 | Steenhoek et al. | |
| 8,743,364 B2 | 6/2014 | Krause et al. | |

(Continued)

FOREIGN PATENT DOCUMENTS

| | | | |
|---|---|---|---|
| DE | 102020100407 A1 * | 7/2020 | ......... B23Q 17/0904 |
| EP | 0335192 A2 | 10/1989 | |

(Continued)

OTHER PUBLICATIONS

Elcometer Inspection Equipment, "Introducing the Elcometer 480 Single, Dual and Triple Angle Glossmeter", https://www.youtube.com/watch?v=6hWv9jOjHrw Sep. 15, 2014 (Year: 2014).*

(Continued)

*Primary Examiner* — Maurice C Smith
(74) *Attorney, Agent, or Firm* — Lorenz & Kopf, LLP (57) ABSTRACT

Methods and systems for matching color and/or appearance of a surface of an object are provided. In one example, method includes determining a gloss of the surface of the object at one or more angles. The gloss is compared to a minimum gloss threshold to determine a condition of the surface of the object. If the gloss is at or exceeds the minimum gloss threshold, the surface is properly conditioned. If the gloss is less than the minimum gloss threshold, the surface is improperly conditioned. The color and/or appearance of the surface of the object is characterized if the surface is properly conditioned.

16 Claims, 5 Drawing Sheets

(56) References Cited

U.S. PATENT DOCUMENTS

| | | |
|---|---|---|
| 8,771,785 B2 | 7/2014 | Steenhoek et al. |
| 8,909,574 B2 | 12/2014 | Mohammadi et al. |
| 8,929,646 B2 | 1/2015 | Rodrigues et al. |
| 8,999,429 B2 | 4/2015 | Steenhoek et al. |
| 9,080,915 B2 | 7/2015 | Krause et al. |
| 9,292,744 B2 | 3/2016 | Rodrigues et al. |
| 9,677,942 B2 | 6/2017 | Steenhoek |
| 10,928,327 B2 | 2/2021 | Steenhoek et al. |
| 11,062,479 B2 | 7/2021 | Steenhoek et al. |
| 11,080,552 B2 | 8/2021 | Steenhoek et al. |
| 2013/0154830 A1 | 6/2013 | Xu et al. |
| 2021/0381896 A1 | 12/2021 | Xu et al. |

FOREIGN PATENT DOCUMENTS

| | | | | |
|---|---|---|---|---|
| EP | 3384831 A1 | * | 10/2018 | ........... A61B 5/0075 |
| WO | WO-2010121913 A1 | * | 10/2010 | .......... B41F 33/0036 |
| WO | WO-2020262615 A1 | * | 12/2020 | |
| WO | WO-2023161235 A1 | * | 8/2023 | |

OTHER PUBLICATIONS

Datacolor, "Reliable Color Measurement" Jan. 1, 2017: pp. 1-2.
Lasseter Clare et al. "Characterization of High Performance Protective Coatings for use on Culturally Significant Works" Jan. 1, 2021: pp. 1-20.

* cited by examiner

| Gloss Indicator | 45° Value |
|---|---|
| Grey Coating High Gloss | 61 |
| Grey Coating Matt | 23 |
| Delta Gloss | 38 |

FIG. 5

| Color | L*15 | a*15 | b*15 | L*45 | a*45 | b*45 | L*110 | a*110 | b*110 |
|---|---|---|---|---|---|---|---|---|---|
| Unprepared | 123.88 | -0.11 | 2.82 | 66.17 | -0.13 | 0.13 | 35.83 | -1.02 | -0.84 |
| Prepared | 123.87 | -0.01 | 3.08 | 65.49 | -0.13 | 0.00 | 34.84 | -1.11 | -1.09 |
| Delta E* | 0.27 | | | 0.69 | | | 1.02 | | |

FIG. 6A

| Gloss Indicator | 45° Value |
|---|---|
| Unprepared | 54 |
| Prepared | 60 |
| Delta Gloss | 6 |

FIG. 6B

| Color | L*15 | a*15 | b*15 | L*45 | a*45 | b*45 | L*110 | a*110 | b*110 |
|---|---|---|---|---|---|---|---|---|---|
| Unprepared | 75.86 | -0.21 | 3.32 | 34.66 | -0.32 | 0.18 | 15.51 | -0.56 | -2.48 |
| Prepared | 75.72 | -0.49 | 3.11 | 36.45 | -0.28 | 0.37 | 14.77 | -0.59 | -2.72 |
| Delta E* | 0.38 | | | 1.8 | | | 0.77 | | |

FIG. 7A

| Gloss Indicator | 45° Value |
|---|---|
| Unprepared | 56 |
| Prepared | 62 |
| Delta Gloss | 6 |

FIG. 7B

| Color | L*15 | a*15 | b*15 | L*45 | a*45 | b*45 | L*110 | a*110 | b*110 |
|---|---|---|---|---|---|---|---|---|---|
| Unprepared | 26.39 | 0.07 | -2.72 | 8.70 | 0.08 | -1.54 | 5.13 | -0.07 | -0.94 |
| Prepared | 20.63 | 0.01 | -3.40 | 5.90 | -0.06 | -1.33 | 3.40 | -0.09 | -0.77 |
| Delta E* | 5.81 | | | 2.81 | | | 1.74 | | |

FIG. 8A

| Gloss Indicator | 45° Value |
|---|---|
| Unprepared | 57 |
| Prepared | 61 |
| Delta Gloss | 4 |

FIG. 8B

| Color | L*15 | a*15 | b*15 | L*45 | a*45 | b*45 | L*110 | a*110 | b*110 |
|---|---|---|---|---|---|---|---|---|---|
| Clean | 80.17 | -13.44 | 11.59 | 79.37 | -13.61 | 12.11 | 78.31 | -13.10 | 11.31 |
| Fingerprint | 81.60 | -12.92 | 11.57 | 79.47 | -13.54 | 12.29 | 78.60 | -13.04 | 11.50 |
| Delta E* | 1.53 | | | 0.22 | | | 0.35 | | |

FIG. 9A

| Gloss Indicator | 45° Value |
|---|---|
| Clean | 59 |
| Fingerprint | 51 |
| Delta Gloss | 8 |

FIG. 9B

| Color | L*15 | a*15 | b*15 | L*45 | a*45 | b*45 | L*110 | a*110 | b*110 |
|---|---|---|---|---|---|---|---|---|---|
| Clean | 92.80 | -1.39 | 1.39 | 92.30 | -1.46 | 1.52 | 91.00 | -1.48 | 1.13 |
| Fingerprint | 94.96 | -1.17 | 1.25 | 92.34 | -1.43 | 1.59 | 91.12 | -1.45 | 1.20 |
| Delta E* | 2.17 | | | 0.08 | | | 0.14 | | |

FIG. 10A

| Gloss Indicator | 45° Value |
|---|---|
| Clean | 60 |
| Fingerprint | 52.5 |
| Delta Gloss | 7.5 |

FIG. 10B

METHOD AND SYSTEM FOR MATCHING COLOR AND/OR APPEARANCE OF A SURFACE

TECHNICAL FIELD

The technical field relates generally to coatings and/or surfaces having color and/or appearance characteristics, and more particularly to methods and systems for matching color and/or appearance of a surface of an object, such as, for example, a component panel with a surface coating that forms at least part of the surface, a calibration tile for calibrating a color and/or appearance characterization device, or the like.

BACKGROUND

Surface coatings such as monocoats, clearcoats/colorcoats, and tricoats are favored for the protection and decoration of substrates such as vehicle or component body panels. The surface coatings can utilize one or more pigments or effect pigments to impart the desired color and/or appearance, such as solid, metallic, pearlescent effect, gloss, or distinctness of image, to the vehicle bodies. Metallic flakes, such as aluminum flakes are commonly used to produce coatings having flake appearances such as texture, sparkle, glint, coarseness and glitter as well as the enhancement of depth perception in the coatings imparted by the flakes.

Repair of such coatings that have been damaged, e.g., in a collision or stone chipping or scratches, has been difficult in that a vehicle repair body shop or a refinisher may have to go to great lengths to repeatedly try out and to locate a best aftermarket refinish coating composition that matches the color and appearance of the vehicle's original coating, also known as original equipment manufacturing (OEM) coating. While each coating composition used in a vehicle's OEM coating is manufactured to a given color standard, so that, in theory, all vehicles painted with a given coating composition should appear the same color and appearance, due to a host of different variables, such as changing atmospheric conditions and use of different application techniques, the color and/or appearance of a given coating composition may actually vary from plant to plant and over different times of any given year. Consequently, vehicles manufactured at one plant may appear a different color than vehicles painted with the same coating composition at another plant. In addition, a vehicle's OEM coating may also change color or appearance due to environmental exposure and time. A number of refinish matching coating compositions must therefore be developed for each OEM coating composition. Presently there is no quick, easy and inexpensive way to determine which aftermarket matching refinish coating composition is the best match in color and appearance for a particular OEM coating.

Various color matching techniques have been developed in the past to aid in the selection of the correct matching coating composition to refinish a vehicle, but all have certain significant limitations. For example, a body shop may make color and/or appearance measurements of a damaged coating to search a database of various OEM coatings in which the OEM coatings in the database are in pristine condition. Prior to making any measures, the body shop may prep the surface of the damaged coating, which may be weathered, dirty, or the like. However, if the surface of the damaged coating has been improperly or inadequately prepped, or not prepped at all, this can lead to measurement offsets, which can make the formula retrieval process less reliable. Administrative procedures and directions are often put in place to minimize the problem of improper surface preparation. However, it is difficult to monitor in a practical sense whether or not such procedures and/or directions have been followed.

Accordingly, it is desirable to provide methods and systems that address one or more of the foregoing issues. Furthermore, other desirable features and characteristics of the present disclosure will become apparent from the subsequent detailed description and the appended claims, taken in conjunction with this background.

SUMMARY

Methods and systems for matching color and/or appearance of a surface of an object are provided herein. In accordance with an exemplary embodiment, the method includes determining a gloss of the surface of the object at one or more angles. The gloss is compared to a minimum gloss threshold to determine a condition of the surface of the object. If the gloss is at or exceeds the minimum gloss threshold, the surface is properly conditioned. If the gloss is less than the minimum gloss threshold, the surface is improperly conditioned. The color and/or appearance of the surface of the object is characterized if the surface is properly conditioned.

In accordance with an exemplary embodiment, the system includes a gloss meter for making one or more gloss measurements of the surface of the object to determine the gloss of the surface. A computer arrangement includes a processor and is operative to compare the gloss to a minimum gloss threshold to determine a condition of the surface of the object. If the gloss is at or exceeds the minimum gloss threshold, the surface is properly conditioned. If the gloss is less than the minimum gloss threshold, the surface is improperly conditioned. A color and/or appearance characterization device is configured to characterize the color and/or appearance of the surface of the object if the surface is properly conditioned.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

A vehicle "component," as used herein, includes a plastic or polymeric substrate with an overlying coating. The term "overlying," as used herein, means the overlying material may be physically touching the underlying substrate, or the overlying material may be physically separated from the underlying substrate by an intervening material, such as an overlying layer that may be separated from an underlying substrate by another layer. It is understood that a component may be rotated or moved, so reference to one component overlying another refers to a particular orientation, with the understanding that the actual component may be rotated into a different orientation. The term "vehicle," as used herein, refers to a motor vehicle, such as a car, truck, airplane, or other device propelled through space with a motor or engine. The term vehicle includes vehicles propelled by a motor burning fuel for power, and a vehicle propelled by an engine using electricity. The overlying coating of the component includes one or more of a primer, a basecoat, and a clearcoat.

Various embodiments contemplated herein relate to methods and systems for matching color and/or appearance of a surface of an object. The exemplary embodiments taught herein include determining a gloss of the surface of the object at one or more angles. The gloss is compared to a minimum gloss threshold, which may be color or coating dependent, to determine a condition of the surface of the object. If the gloss is at or exceeds the minimum gloss threshold, the surface is properly conditioned. If the gloss is less than the minimum gloss threshold, the surface is improperly conditioned. The color and/or appearance of the surface of the object is characterized if the surface is properly conditioned. In an exemplary embodiment, Applicants have found that by characterizing the surface of the object after ensuring that the surface is properly conditioned, the surface, for example, of a damaged coating will produce color and/or appearance measurements that reduce, minimize, or eliminate any offsets when searching a database of various coatings that are in pristine condition to aid in the selection of the correct matching coating composition to refinish the surface of the object.

Figure 1:
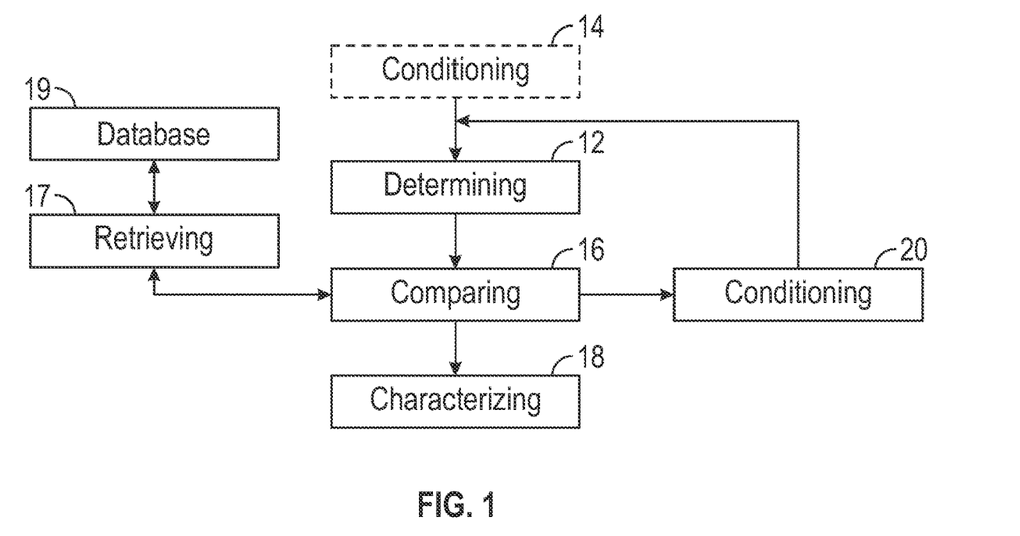
FIG. 1 illustrates a block diagram of a method for matching color and/or appearance of a surface of an object in accordance with an exemplary embodiment.

FIG. 1 illustrates a method 10 for matching color and/or appearance of a surface of an object in accordance with an exemplary embodiment. The object may be a vehicle or component body panel or other object with a surface coating, a color calibration tile, or the like.

The method 10 includes determining (STEP 12) a gloss of the surface of the object at one or more angles. In an exemplary embodiment, the gloss of the surface is measured with a gloss meter at one or more angles. Gloss meters are well known in the art. Commercially available gloss meters are sold, for example, by BYK-Gardner Inc. as well as by other manufactures. The gloss of the surface may be measured at one or more angles between 0 and 180° and/or at a plurality of locations proximate to each other. In an exemplary embodiment, the gloss is measured at one or more angles selected from 15°, 45°, 60°, and/or 110°. In an exemplary embodiment, a plurality of gloss measurements are taken of the surface at one or more angles and/or at one or more locations proximate to each other to determine an average value that defines the gloss.

In an exemplary embodiment, prior to determining the gloss the surface of the object, the surface of the object is conditioned (STEP 14). In one example, the object is a component and the surface includes a surface coating. The surface is conditioned by polishing the surface coating, for example, by using various grades of polishing compound that are rubbed and subsequently removed from the surface coating to bring the gloss of the surface coating up sequentially to or towards the surface coatings nominal or target gloss when the surface coating is in pristine condition.

The method 10 continues by comparing (STEP 16) the gloss to a minimum gloss threshold to determine a condition of the surface of the object. As discussed above, in the example where the object is a component with a surface coating, the surface coating defines a target coating. The method 10 includes retrieving (STEP 17) color characteristics of the target coating and the minimum gloss threshold and/or a target gloss associated with the target coating from a formula or component database 19. The minimum gloss threshold may be provided from the formula or component database 19 or alternatively, may be calculated by subtracting a predetermined value from the target gloss.

As will be discussed in further detail below, in an exemplary embodiment, the predetermined value is about 2 or greater than about 2. For example, the target coating retrieved from the formula or component database 19 may have a specific color, e.g., grey metallic, black metallic, or the like, which has a corresponding target gloss value and predetermined value associated with the specific color. If the target gloss value is, for example, 60 when measured at 45° and the predetermined value is 2, the minimum gloss threshold is 58 when measured at 45°. In another example, if the target gloss value is, for example, 65 when measured that 60° and the predetermined value is 3, the minimum gloss threshold is 62 when measured at 60°.

If the gloss is at or exceeds the minimum gloss threshold, the surface is properly conditioned. For example, if the minimum gloss threshold is 58 when measured at 45° and the gloss of the surface of the object is 58 or greater than 58 when measured at 45°, then the surface is properly conditioned. Likewise, if the gloss is less than the minimum gloss threshold, the surface is improperly conditioned. For example, if the minimum gloss threshold is 62 when measured at 60° and the gloss of the surface of the object is less than 62 when measured at 60°, then the surface is improperly conditioned and, as will be discussed in further detail below, further conditioning is needed to increase the gloss of the surface to at or above the minimum gloss threshold to indicate a properly conditioned surface.

In an exemplary embodiment, the method 10 continues by characterizing (STEP 18) the color and/or appearance of the surface of the object if the surface is properly conditioned. In particular, by characterizing the surface of the object after ensuring that the surface is properly conditioned, the surface, for example, of a damaged coating will produce color and/or appearance measurements that reduce, minimize, or eliminate any offsets when searching a database of various coatings that are in pristine condition to aid in the selection of the correct matching coating composition to refinish the surface of the object. Non-limiting examples of methods and systems for characterizing the color and/or appearance of a surface and for searching and retrieving a database of various coating are described in U.S. Pat. No. 8,441,641, filed on Apr. 21, 2011, U.S. Pat. No. 8,999,429, filed on Jan. 14, 2014, U.S. Pat. No. 8,909,574, filed on Dec. 18, 2013, U.S. Pat. No. 8,929,646, filed on Jun. 24, 2011, U.S. Pat. No. 9,080,915, filed on May 1, 2014, U.S. Pat. No. 9,292,744, filed on Jun. 24, 2011, U.S. Pat. No. 9,677,942, filed on Oct. 30, 2014, U.S. Pat. No. 10,928,327, filed on Dec. 11, 2017, U.S. Pat. No. 11,062,479, filed on Dec. 6, 2017, and U.S. Pat. No. 11,080,552, filed on Aug. 29, 2019, which are owned by the assignee of the present application and are hereby incorporated by reference in their entirety for all purposes.

In an exemplary embodiment, the color and/or appearance is characterized by measuring the surface of the object with a color and/or appearance characterization device. Examples of color and/or appearance characterization devices includes spectrophotometers, colorimeters, and the like. Further, color characteristics can include, but are not limited to, L, a, b values, L*, a*, b* values, X, Y, Z values, L, C, h values, spectral reflectance data, modified spectral reflectance data, or combinations thereof. Appearance characteristics can include, but are not limited to, texture, metallic, pearlescent effect, gloss, distinctness of image, flake appearances such as texture, sparkle, glint, coarseness and glitter as well as the enhancement of depth perception in the coatings imparted by the flakes, especially produced by metallic flakes, such as aluminum flakes.

As discussed above, in an exemplary embodiment, if the surface is improperly conditioned, for example, the surface has a gloss of less than the minimum gloss threshold, the surface is conditioned (STEP 20) to raise the gloss of the surface. For instance, if the surface includes a surface coating, conditioning may include polishing the surface with various grades of polishing compound that are rubbed and subsequently removed from the surface coating to bring the gloss of the surface coating up sequentially to or towards the surface coatings nominal or target gloss when the surface coating is in pristine condition. In another example, if the object is a calibration tile for calibrating a color and/or appearance characterization device (e.g., used for adjusting device settings (e.g., signal gains) for calibrating the device), conditioning the surface may include cleaning the surface to bring the gloss of the surface up to the surface's nominal or target gloss.

After conditioning, the method 10 continues by determining (STEP 12) the corresponding gloss of the surface of the object at one or more angles and comparing (STEP 16) the corresponding gloss to the minimum gloss threshold to determine the condition of the surface of the object. If the corresponding gloss exceeds the minimum gloss threshold, the surface is properly conditioned and the method continues by characterizing (STEP 18) the color and/or appearance of the surface of the object as discussed above. Alternatively, if the corresponding gloss is less than the minimum gloss threshold, the surface is improperly conditioned and the method 10 continues by repeating the steps of conditioning (STEP 20) the surface, determining (STEP 12) the corresponding gloss and comparing (STEP 16) to the minimum gloss threshold until the surface is properly conditioned. Once the surface is properly conditioned, then the color and/or appearance of the surface of the object is characterized (STEP 18).

Figure 2:
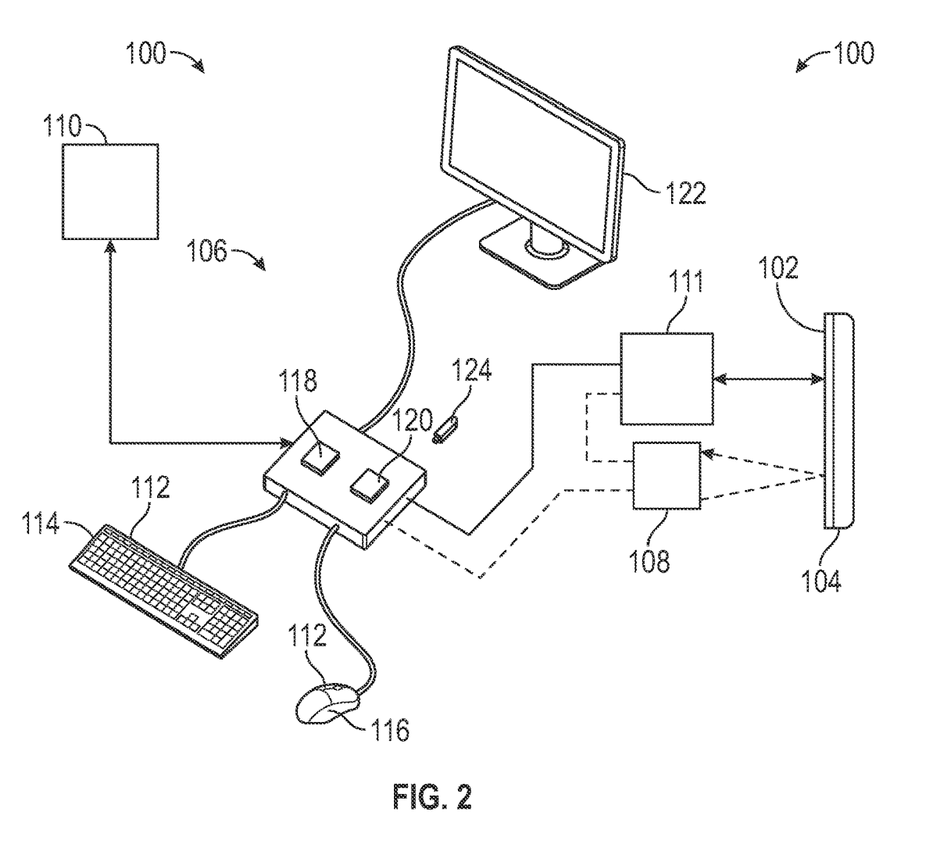
FIG. 2 illustrates a perspective view of a system for matching color and/or appearance of a surface of an object in accordance with an exemplary embodiment.

FIG. 2 illustrates a perspective view of a system 100 for matching color and/or appearance of a surface 102 of an object 104 in accordance with an exemplary embodiment. The system 100 includes a computer 106, which may be used as a device to implement the techniques and methods described herein. The computer 106 may include an input device 112, such as a keyboard 114, a mouse 116, electronic communication devices such as a modem, or a variety of other communication devices. The input device 112 communicates with a processor 118 (processing unit) and/or a memory 120 of the computer, where the processor 118 and the memory 120 communicate with each other. A wide variety of processor 118 and memory 120 embodiments are known to those skilled in the art. The computer 100 also includes an output device 122, such as the monitor illustrated. Other exemplary embodiments of an output device 122 include a modem, a printer, or other components known to those skilled in the art. The methods and techniques described above may be implemented on the computer 100.

A computer readable medium 124 embodies a computer or software program, where the computer program directs the computer to implement the method and techniques described above. The computer readable medium may be an SD card, a USB storage medium, a floppy disk, a CD-ROM, a DVD, a hard drive, or other devices that are readable by the computer 106, and that include memory for saving the computer program. In some embodiments, the computer program may be electronically downloaded to the computer, but the downloaded computer program is saved on a tangible device somewhere.

In an exemplary embodiment, the computer program directs the computer to request input from the input device 112, wherein the requested input is directed towards obtaining one or more gloss measurements of the surface 102 of the object 104 from a gloss meter 108 to determine the gloss of the surface 102. Alternatively, the user may manually input the one or more gloss measurements via the input device 112.

The computer program directs the processor 118 to compare the gloss to a minimum gloss threshold, for example retrieved from the formula or component database 110 or otherwise calculated as discussed above, to determine the condition of the surface of the object. For example, using the processor, color and/or appearance characteristics of a target coating and one of the minimum gloss threshold and a target gloss associated with the target coating are retrieved from the formula or component database 110. If the gloss is at or exceeds the minimum gloss threshold, the surface 102 is properly conditioned, and if the gloss is less than the minimum gloss threshold, the surface 102 is improperly conditioned.

In an exemplary embodiment, if the surface 102 is properly conditioned, the computer program directs the computer 106 to request input from the input device 112, wherein the requested input is directed towards a color and/or appearance characterization device 112 to characterize the color and/or appearance of the surface 102 of the object 104. In the event that the surface 102 is improperly conditioned, the computer 106 alerts, for example via the output device 122, the user that the surface requires conditioning as discussed above before repeating the gloss and color and/or appearance measurements.

As illustrated, the gloss meter 108 may be a stand-alone device separate from the color and/or appearance characterization device 111. Alternatively, the gloss meter 108 may be integrated into or otherwise combined with the color and/or appearance characterization device 111.

The following examples are provided for illustration purposes only and are not meant to limit the various embodiments of the coating composition in any way.

Examples

Figure 3:
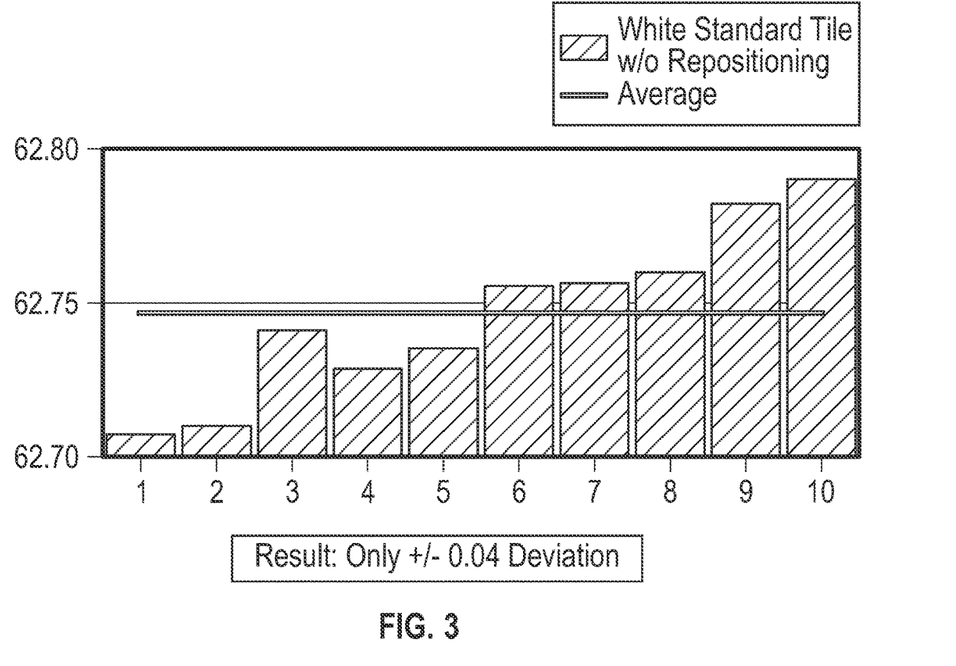
FIG. 3 illustrates a graphical representation of a plurality of gloss measurements of a surface of an object without repositioning in accordance with an exemplary embodiment.

Referring to FIG. 3, a plurality of gloss measurements at 45° of a surface of an object without repositioning in accordance with an exemplary embodiment is provides. As illustrated, 10 consecutive gloss measurements of a white standard tile without repositioning were measured. The results indicated a standard deviation of only +/−0.04, thus indicating minimal gloss variation due to the instrument, e.g., gloss meter, itself.

Figure 4:
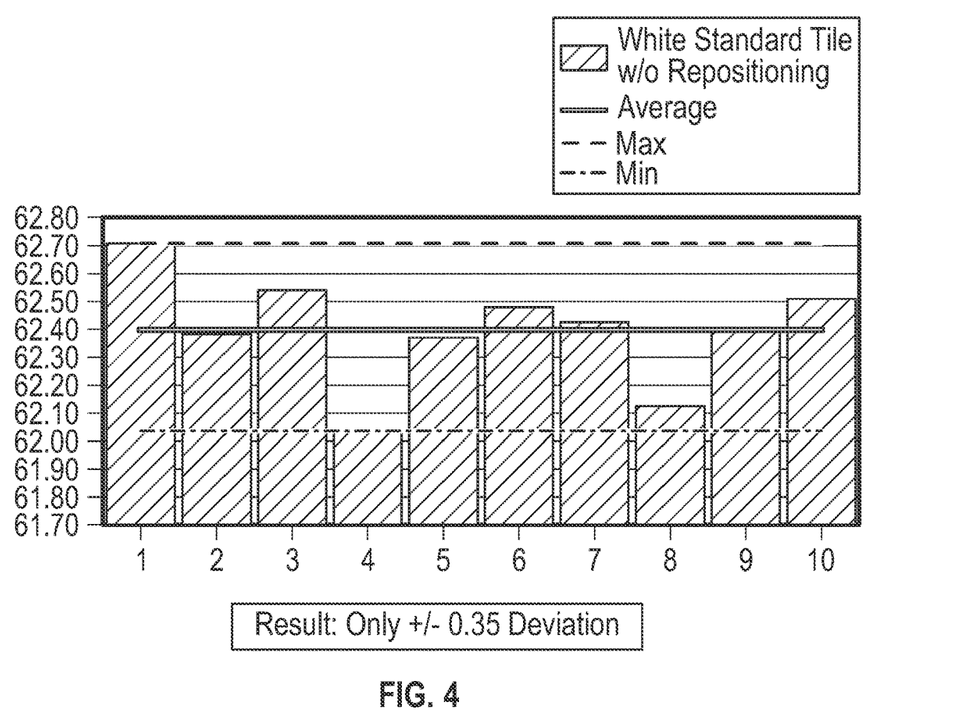
FIG. 4 illustrates a graphical representation of a plurality of gloss measurements of a surface of an object with repositioning in accordance with an exemplary embodiment.

Referring to FIG. 4, a plurality of gloss measurements at 45° of a surface of an object with repositioning in accordance with an exemplary embodiment is provided. As illustrated, 10 consecutive gloss measurements of a white standard tile with repositioning were measured. The results indicate a standard deviation of only +/−0.35, which although is an order of magnitude greater than the results illustrated indicated in FIG. 3, it is still relatively small compared to the average gloss values, thus indicating relatively small variations due to gloss measurements taken at locations that are proximate to each other.

Figure 5:
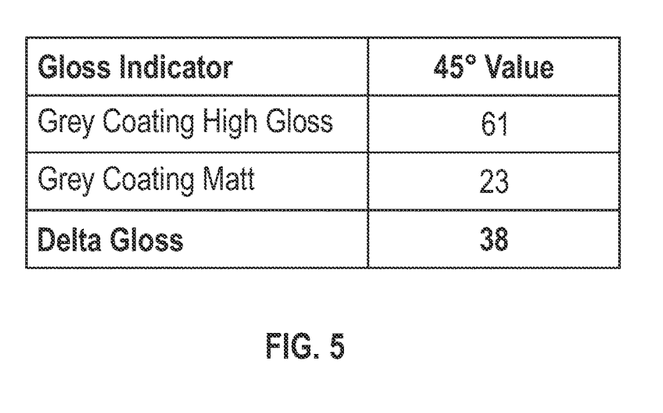
FIG. 5 illustrates a table of gloss measurements of a grey coating with a high gloss finish versus a grey coating with a matt finish in accordance with an exemplary embodiment.

Referring to FIG. 5, gloss measurements at 45° of a grey coating with a high gloss finish versus a grey coating with a matt finish in accordance with an exemplary embodiment are provided. As illustrated, the delta gloss between the gray coating with the high gloss finish (e.g., gloss of 61) and the gray coating with the matt finish (e.g., gloss of 23) is 38, thus indicating the substantial difference or delta (e.g., 3 orders of magnitude greater than the standard deviation due to the gloss meter as illustrated in FIG. 2) between a high gloss finish and a matt finish.

Figure 6A:
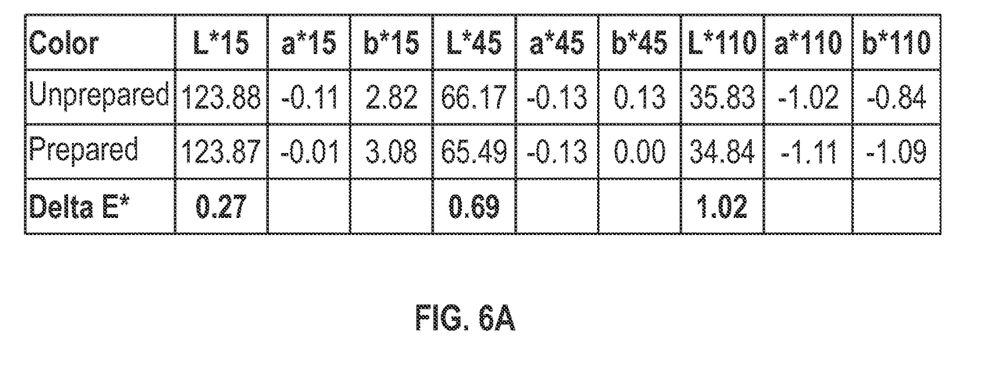
FIG. 6A illustrates a table of color and/or appearance measurements of a silver metallic coating in accordance with an exemplary embodiment.
Figure 6B:
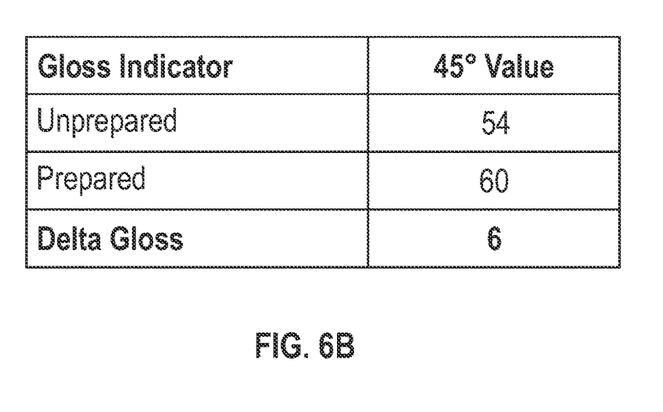
FIG. 6B illustrates a table of gloss measurements of a silver metallic coating with an unprepared surface versus a prepared surface in accordance with an exemplary embodiment.

Referring to FIGS. 6A-6B, a table of color and/or appearance measurements of a silver metallic coating and a table of gloss measurements at 45° of a silver metallic coating with an unprepared surface versus a prepared surface, respectively, are provided. As illustrated, the delta E* values between the unprepared or improperly conditioned surface and the prepared or properly conditioned surface ranges of 0.27 and 1.02. A delta E* value of about 1 or great indicates a visibly discernible color and/or appearance mismatch. Further, the delta gloss between the unprepared or improperly conditioned surface and the prepared or properly conditioned surface is 6, thus indicating that if the nominal or target gloss of the silver metallic coating is 60, a minimum gloss threshold of from about 55 to about 58 (e.g., a predetermined value of about 2 to about 5) would be sufficient to identify that the unprepared or improperly conditioned surface requires further conditioning prior to characterizing its color and/or appearance.

Figure 7A:
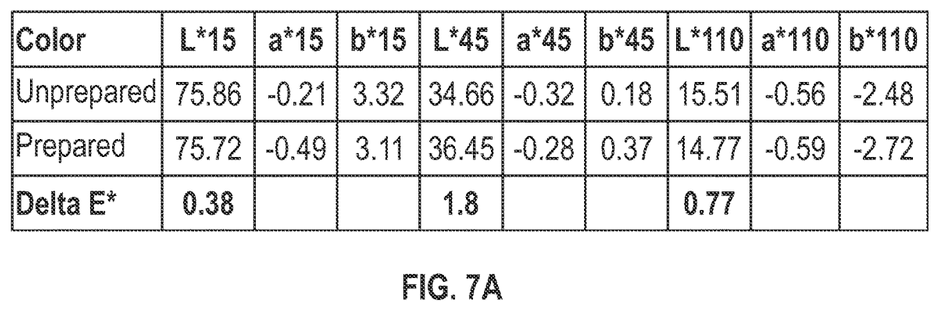
FIG. 7A illustrates a table of color and/or appearance measurements of a grey metallic coating in accordance with an exemplary embodiment.
Figure 7B:
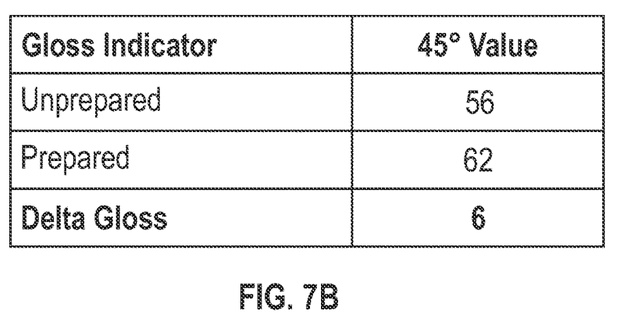
FIG. 7B illustrates a table of gloss measurements of a grey metallic coating with an unprepared surface versus a prepared surface in accordance with an exemplary embodiment.

Referring to FIGS. 7A-7B, a table of color and/or appearance measurements of a grey metallic coating and a table of gloss measurements at 45° of a grey metallic coating with an unprepared surface versus a prepared surface, respectively, are provided. As illustrated, the delta E* values between the unprepared or improperly conditioned surface and the prepared or properly conditioned surface ranges of 0.38 and 1.8. A delta E* value of about 1 or great indicates a visibly discernible color and/or appearance mismatch. Further, the delta gloss between the unprepared or improperly conditioned surface and the prepared or properly conditioned surface is 6, thus indicating that if the nominal or target gloss of the silver metallic coating is 62, a minimum gloss threshold of from about 57 to about 60 (e.g., a predetermined value of about 2 to about 5) would be sufficient to identify that the unprepared or improperly conditioned surface requires further conditioning prior to characterizing its color and/or appearance.

Figure 8A:
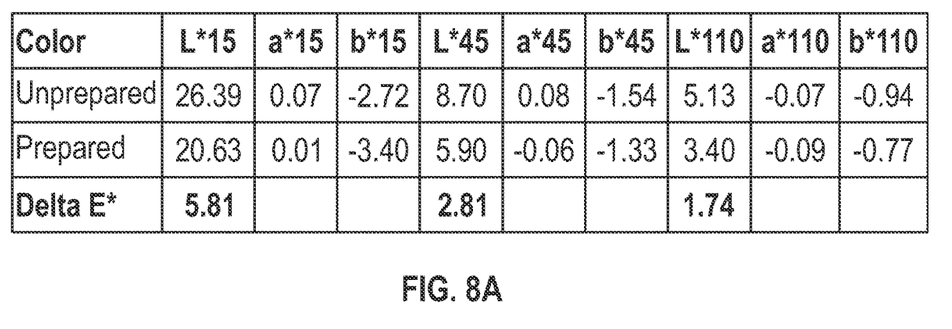
FIG. 8A illustrates a table of color and/or appearance measurements of a black metallic coating in accordance with an exemplary embodiment.
Figure 8B:
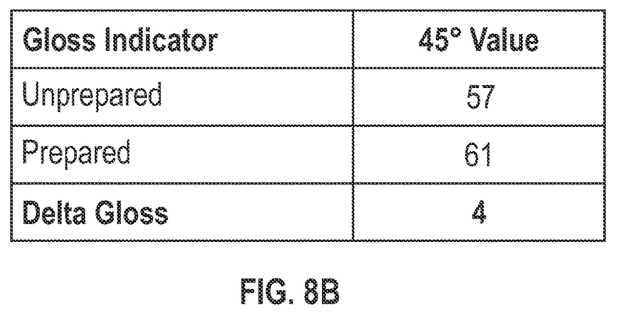
FIG. 8B illustrates a table of gloss measurements of a black metallic coating with an unprepared surface versus a prepared surface in accordance with an exemplary embodiment.

Referring to FIGS. 8A-8B, a table of color and/or appearance measurements of a black metallic coating and a table of gloss measurements at 45° of a black metallic coating with an unprepared surface versus a prepared surface, respectively, are provided. As illustrated, the delta E* values between the unprepared or improperly conditioned surface and the prepared or properly conditioned surface ranges of 1.74 and 5.81. A delta E* value of about 1 or great indicates a visibly discernible color and/or appearance mismatch. Further, the delta gloss between the unprepared or improperly conditioned surface and the prepared or properly conditioned surface is 4, thus indicating that if the nominal or target gloss of the silver metallic coating is 61, a minimum gloss threshold of from about 58 to about 59 (e.g., a predetermined value of about 2 to about 3) would be sufficient to identify that the unprepared or improperly conditioned surface requires further conditioning prior to characterizing its color and/or appearance.

Figure 9A:
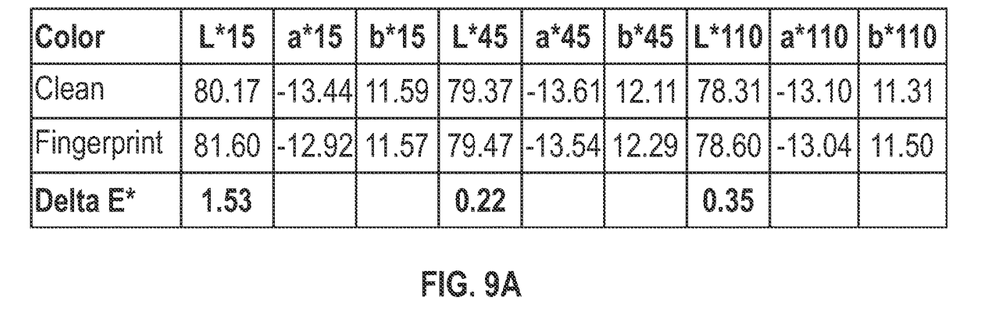
FIG. 9A illustrates a table of color and/or appearance measurements of a color check tile with a clean surface versus a fingerprinted surface in accordance with an exemplary embodiment.
Figure 9B:
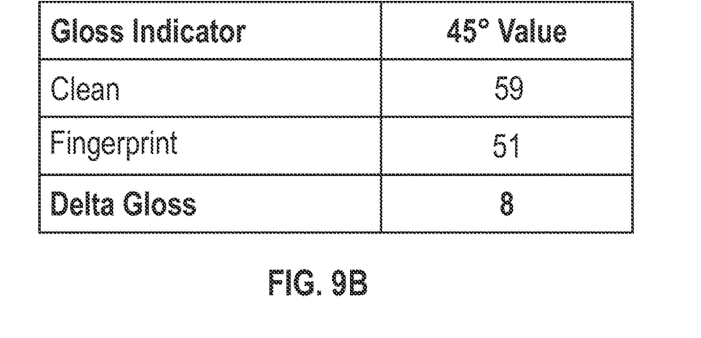
FIG. 9B illustrates a table of gloss measurements of a color check tile with a clean surface versus a fingerprinted surface in accordance with an exemplary embodiment.

Referring to FIGS. 9A-9B, a table of color and/or appearance measurements of a color check tile with a clean surface versus a fingerprinted surface and a table of gloss measurements at 45° of a color check tile with a clean surface versus a fingerprinted surface, respectively, are provided. As illustrated, the delta E* values between the fingerprinted or improperly conditioned surface and the clean or properly conditioned surface ranges of 0.22 and 1.53. A delta E* value of about 1 or great indicates a visibly discernible color and/or appearance mismatch. Further, the delta gloss between the fingerprinted or improperly conditioned surface and the clean or properly conditioned surface is 8, thus indicating that if the nominal or target gloss of the silver metallic coating is 59, a minimum gloss threshold of from about 52 to about 57 (e.g., a predetermined value of about 2 to about 7) would be sufficient to identify that the fingerprinted or improperly conditioned surface requires further conditioning prior to characterizing its color and/or appearance.

Figure 10A:
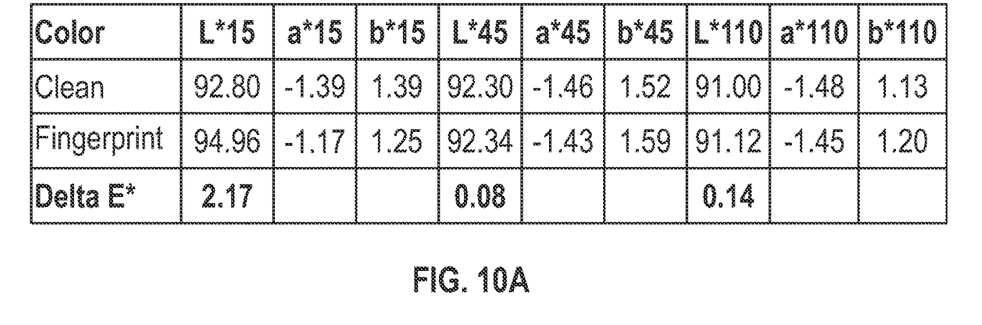
FIG. 10A illustrates a table of color and/or appearance measurements of a white standard tile with a clean surface versus a fingerprinted surface in accordance with an exemplary embodiment.
Figure 10B:
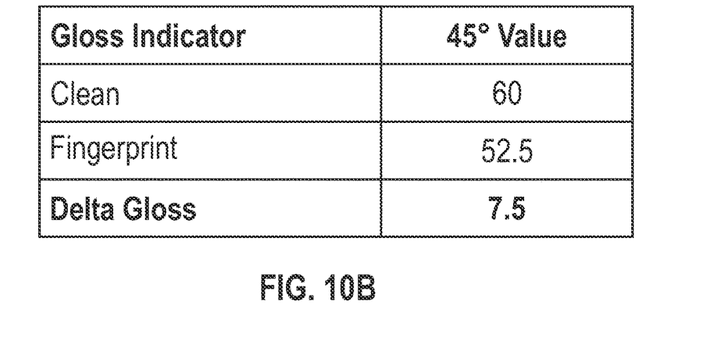
FIG. 10B illustrates a table of gloss measurements of a white standard tile with a clean surface versus a fingerprinted surface in accordance with an exemplary embodiment.

Referring to FIGS. 10A-10B, a table of color and/or appearance measurements of a white standard tile with a clean surface versus a fingerprinted surface and a table of gloss measurements at 45° of a white standard tile with a clean surface versus a fingerprinted surface, respectively, are provided. As illustrated, the delta E* values between the fingerprinted or improperly conditioned surface and the clean or properly conditioned surface ranges of 0.08 and 2.17. A delta E* value of about 1 or great indicates a visibly discernible color and/or appearance mismatch. Further, the delta gloss between the fingerprinted or improperly conditioned surface and the clean or properly conditioned surface is 7.5, thus indicating that if the nominal or target gloss of the silver metallic coating is 60, a minimum gloss threshold of from about 53.5 to about 58 (e.g., a predetermined value of about 2 to about 6.5) would be sufficient to identify that the fingerprinted or improperly conditioned surface requires further conditioning prior to characterizing its color and/or appearance.

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It is understood that various changes may be made in the function and arrangement of elements described in an exemplary embodiment without departing from the scope of the disclosure as set forth in the appended claims.

What is claimed is:

1. A method for matching color and/or appearance of a surface of an object, the method comprising the steps of:
    taking a plurality of gloss measurements of the surface of the object at one or more angles between 0 and 180° and/or at a plurality of locations proximate to each other, using a gloss meter;
    determining an average value of the plurality of measurements that defines the gloss, using the gloss meter;
    comparing the gloss to a minimum gloss threshold, using a computer arrangement including a processor, to determine a condition of the surface of the object, wherein if the gloss is at or exceeds the minimum gloss threshold, the surface is properly conditioned, and wherein if the gloss is less than the minimum gloss threshold, the surface is improperly conditioned; and
    characterizing the color and/or appearance of the surface of the object, using a characterization device, to produce color and/or appearance measurements if the surface is properly conditioned.

2. The method of claim 1, further comprising the steps of;
    conditioning the surface of the object if the surface is improperly conditioned;
    determining a corresponding gloss of the surface of the object at one or more angles after conditioning; and
    comparing the corresponding gloss to the minimum gloss threshold to determine the condition of the surface of the object, wherein if the corresponding gloss exceeds the minimum gloss threshold, the surface is properly conditioned.

3. The method of claim 2, wherein if the corresponding gloss is less than the minimum gloss threshold, the surface is improperly conditioned and the method including repeating the steps of conditioning the surface, determining the corresponding gloss and comparing to the minimum gloss threshold until the surface is properly conditioned.

4. The method of claim 2, wherein the surface includes a surface coating, and wherein conditioning the surface comprises polishing the surface coating.

5. The method of claim 2, wherein conditioning the surface comprises cleaning the surface.

6. The method of claim 1, further comprising the step of conditioning the surface of the object prior to determining the gloss of the surface.

7. The method of claim 1, wherein determining the gloss comprises measuring the gloss at the one or more angles selected from 15°, 45°, 60°, 110°, or combinations thereof.

8. The method of claim 1, wherein characterizing the color and/or appearance comprises measuring the surface of the object with a color and/or appearance characterization device.

9. The method of claim 8, wherein the color and/or appearance characterization device includes a spectrophotometer or a colorimeter.

10. A method for matching color and/or appearance of a surface of an object, the method comprising the steps of:
    determining the surface of the object at one or more angles, using a gloss meter;
    comparing the gloss to a minimum gloss threshold, using a computer arrangement including a processor, to determine a condition of the surface of the object, wherein if the gloss is at or exceeds the minimum gloss threshold, the surface is properly conditioned, and wherein if the gloss is less than the minimum gloss threshold, the surface is improperly conditioned; and
    characterizing the color and/or appearance of the surface of the object, using a characterization device, to produce color and/or appearance measurements if the surface is properly conditioned;
    wherein the object is a component, and the surface includes a surface coating that defines a target coating, and the method further comprises retrieving color characteristics of the target coating and one of the minimum gloss threshold and a target gloss associated with the target coating from a formula or component database.

11. The method of claim 10, further comprising calculating the minimum gloss threshold by subtracting a predetermined value from the target gloss.

12. The method of claim 11, wherein the predetermined value is about 2 or greater than about 2.

13. The method of claim 1, wherein the object is a calibration tile for calibrating a color and/or appearance characterization device.

14. A system for matching color and/or appearance of a surface of an object, the system comprising;
    a gloss meter for making one or more gloss measurements of the surface of the object to determine the gloss of the surface;
    a computer arrangement including a processor and operative to compare the gloss to a minimum gloss threshold to determine a condition of the surface of the object, wherein if the gloss is at or exceeds the minimum gloss threshold, the surface is properly conditioned, and wherein if the gloss is less than the minimum gloss threshold, the surface is improperly conditioned;
    a color and/or appearance characterization device configured to characterize the color and/or appearance of the surface of the object and produce color and/or appearance measurements if the surface is properly conditioned; and
    software with a set of instructions for retrieving, using the processor, color characteristics of the target coating and one of the minimum gloss threshold and a target gloss associated with the target coating from a formula or component database;
    wherein the object is a component, and the surface includes a surface coating that defines a target coating.

15. The system of claim 14, wherein the color and/or appearance characterization device includes a spectrophotometer or a colorimeter and the gloss meter is a stand-alone device separate from the color and/or appearance characterization device.

16. The system of claim 14, wherein the color and/or appearance characterization device includes a spectrophotometer or a colorimeter and the gloss meter is combined into the color and/or appearance characterization device.

* * * * *